(12) United States Patent
Tomblin et al.

(10) Patent No.: US 9,919,444 B2
(45) Date of Patent: Mar. 20, 2018

(54) SYSTEM FOR DEVELOPING COMPOSITE REPAIR PATCHES ON AIRCRAFT OR OTHER COMPOSITE STRUCTURES

(71) Applicant: WICHITA STATE UNIVERSITY, Wichita, KS (US)

(72) Inventors: John Tomblin, Wichita, KS (US); Brian M. Brown, Benton, KS (US); Lamia Salah, Andover, KS (US)

(73) Assignee: WICHITA STATE UNIVERSITY, Wichita, KS (US)

( * ) Notice: Subject to any disclaimer, the term of this patent is extended or adjusted under 35 U.S.C. 154(b) by 0 days.

(21) Appl. No.: 14/844,172

(22) Filed: Sep. 3, 2015

(65) Prior Publication Data
US 2017/0008184 A1   Jan. 12, 2017

Related U.S. Application Data

(63) Continuation of application No. 14/795,990, filed on Jul. 10, 2015, now abandoned.

(51) Int. Cl.
*B26D 5/00* (2006.01)
*B32B 43/00* (2006.01)
(Continued)

(52) U.S. Cl.
CPC ............ *B26D 5/007* (2013.01); *B32B 43/003* (2013.01); *B64F 5/40* (2017.01); *A61N 1/025* (2013.01); *B32B 2305/18* (2013.01); *B32B 2305/72* (2013.01); *B32B 2309/68* (2013.01); *B32B 2605/18* (2013.01); *Y10T 29/4973* (2015.01); *Y10T 29/49718* (2015.01); *Y10T 29/49726* (2015.01); *Y10T 29/49732* (2015.01)

(58) Field of Classification Search
CPC .............. G06F 17/50; Y10T 29/49726; Y10T 29/4973; Y10T 29/49718; Y10T 29/49732; A61N 1/025; B26D 5/007; B64F 5/0081; B32B 43/003; B32B 2305/18; B32B 2305/72; B32B 2605/18; B32B 2309/68
See application file for complete search history.

(56) References Cited

U.S. PATENT DOCUMENTS 7,225,050 B2 * 5/2007 Sutula, Jr. .......... G05B 19/4099
                                                      700/117
8,218,852 B2    7/2012 Cork et al.
(Continued)

*Primary Examiner* — John C Hong
(74) *Attorney, Agent, or Firm* — McNair Law Firm, P.A.

(57) ABSTRACT

A system for generating a repair patch for a damaged area of a composite structure may include a scanning module, a repair patch model generator and a cutting tool. The scanning module may be deployed at the location of the damaged composite structure. The scanning module may be configured to scan the damaged area to generate scanned data indicative of a shape, size and/or contours of the damaged area. The repair patch model generator may include processing circuitry configured to obtain the scanned data, obtain parent ply information of the damaged composite structure, and generating a patch model of a repair patch including size and shape definition for each of a plurality of plies based on the scanned data and the parent ply information. The cutting tool may be configured to receive cutting files based on the patch model to generate a plurality of cut plies that combine to form the repair patch.

14 Claims, 7 Drawing Sheets

(51) Int. Cl.
*G06F 17/50* (2006.01)
*B64F 5/00* (2017.01)
*B64F 5/40* (2017.01)
*A61N 1/02* (2006.01)

(56) References Cited

U.S. PATENT DOCUMENTS

| | | |
|---|---|---|
| 8,524,020 B2 | 9/2013 | Lindgren et al. |
| 8,568,545 B2 * | 10/2013 | Lindgren ............... B29C 73/10 |
| | | 156/350 |
| 8,802,213 B2 | 8/2014 | Dan-Jumbo et al. |
| 2008/0281554 A1 * | 11/2008 | Cork ..................... B29C 73/06 |
| | | 702/150 |
| 2012/0080135 A1 * | 4/2012 | Evens ..................... B29C 73/10 |
| | | 156/94 |
| 2012/0330449 A1 * | 12/2012 | Edwards ................ B26D 5/00 |
| | | 700/97 |
| 2013/0068747 A1 * | 3/2013 | Armatorio ............. B64D 15/14 |
| | | 219/202 |

* cited by examiner

SYSTEM FOR DEVELOPING COMPOSITE REPAIR PATCHES ON AIRCRAFT OR OTHER COMPOSITE STRUCTURES

CROSS-REFERENCE TO RELATED APPLICATIONS

This application is a Continuation of U.S. application Ser. No. 14/795,990 filed Jul. 10, 2015, the contents of which are incorporated herein in its entirety.

TECHNICAL FIELD

Example embodiments generally relate to repair techniques on composite structures and, in particular, relate to a technique and system for providing complex and precise repair patches for such structures.

BACKGROUND

Composite repairs require complex and precise repair patches to yield effective strength and durability. The removal of damage and subsequent scarfing can make effective composite repair challenging. In this regard, the individual repair ply shapes required for effective repair can be hard to define and are irregular in shape. Furthermore, contoured surfaces typical of aircraft components (or other composite structures) result in more complexity in the definition of the individual plies and make ply consolidation, a critical step in the manufacturing of an effective repair, difficult. Today's best practices typically use paper or some transparent medium—such as Mylar—as a flat pattern to outline the shape of the repair plies. This process involves tracing and mapping the scarfed parent plies and multiple iterations of fitting and cutting until a best fit is obtained. The paper patterns are then transferred to the raw repair material where orientation and cutting follows. This process is time consuming, operator dependent, and only approximates the outline at best.

Accordingly, it may be desirable to define a process or system by which to cut and consolidate repair patches with greater precision and speed than the current handmade processes. This will result in more robust and cost effective repairs.

BRIEF SUMMARY OF SOME EXAMPLES

Accordingly, some example embodiments may enable the provision of a relatively efficient solution for addressing the issues described above. In particular, some example embodiments may allow a scanner to generate three-dimensional scanned data locally at the composite structure. The scanned data can be used to create cutter files for cutting a plurality (a stack-up) of plies of material of a composite repair patch. These plies may be cut at a remote location and then shipped to the location of the composite structure (e.g., an aircraft component) for application as a repair patch.

In one example embodiment, a system for generating a repair patch for a damaged area of a composite structure is provided. The system may include a scanning module, a repair patch model generator and a cutting tool. The scanning module may be deployed at the location of the composite structure. The scanning module may be configured to scan the damaged area to generate scanned data indicative of a shape, size and/or contours of the damaged area. The repair patch model generator may include processing circuitry configured to obtain the scanned data, parent ply information for the damaged area, and repair patch information including but not limited to size, shape and material definition for each of the repair plies based on the scanned data and the parent ply information. The cutting tool may be configured to receive cutting files based on the patch model to generate a ply stack-up combined to form the repair patch.

In another example embodiment, a method of generating a repair patch for a damaged area of a composite structure is provided. The method may include obtaining scanned data indicative of a shape, size and/or contours of the damaged area of a composite structure, obtaining parent ply information of the damaged composite structure, and generating a model of a repair patch including size and shape definition for of the corresponding repair plies based on the scanned data and the parent ply information.

In yet another example embodiment, an apparatus for generating a repair patch for a damaged area of a composite structure is provided. The apparatus may include processing circuitry configured for obtaining scanned data indicative of shape, size and/or contours of the damaged area of a composite structure, obtaining parent ply information of the damaged composite structure, and generating a model of a repair patch including size and shape definition for each of a plurality of plies based on the scanned data and the parent ply information.

BRIEF DESCRIPTION OF THE SEVERAL VIEWS OF THE DRAWING(S)

Having thus described some examples of the invention in general terms, reference will now be made to the accompanying drawings, which are not necessarily drawn to scale, and wherein:

DETAILED DESCRIPTION

Figure 1:
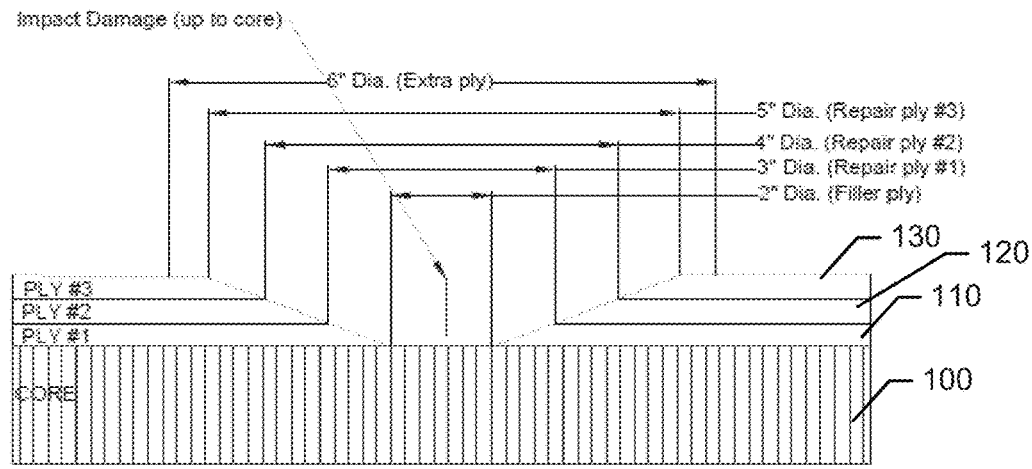
FIG. 1 illustrates a side view of a damaged area that has received impact damage according to an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

In some example embodiments, a system and/or process is provided to couple digital scanning of a damaged area with design and manufacturing equipment to automate and provide greater precision in the building of composite repair patches. As such, some embodiments may be applicable to respond to multiple damage scenarios and complex structures, lay-ups and contours with accuracy and repeatability. Multiple repair techniques using fixed or varying scarf overlaps, fixed or varying scarf ratios, using scarf or step grinding may also be supported. The scanning process is an effective and efficient tool for the geometric development of bonded composite repairs to complex shapes and contours. Although an example embodiment will be described in the context of an aircraft component, it should be appreciated that other composite structures such as wind turbine blades, composite pressure vessels for the oil/gas industry, and/or the like, may also employ the techniques discussed herein with respect to repair patches.

Example embodiments may make repairs available to remote locations far from where the freezers, material and cutting are located. In this regard, a scanner may be brought to the location of a damaged aircraft or to the factory floor. The damage may be removed and the surface nearby may be prepared for repair. Scanned data may be captured and uploaded (e.g., via wired or wireless remote communication) and sent to repair engineers where the appropriate repair materials and stacking sequence are selected. From there, a precision patch may be manufactured and consolidated to be delivered or shipped to the location of the damaged aircraft or to the factory. Some example embodiments may further provide a tool representing the contoured surface of the repaired area so the repair patch can be positioned and consolidated to shape. To maintain the repair patch contour and integrity during shipping or transport, the tools associated with some example embodiments may be manufactured using 3-D printing technologies, or other process, to be shipped with the repair patch.

In some example embodiments, the proposed process could accept repair material identical or different either in form or thickness over the parent material and damage of odd or irregular shapes. A challenging issue that may be encountered during a repair activity is that of integrating differing repair philosophies into a methodology. Some repair processes define the repair by the nature of the machined (sanded) parent substrate after damage removal. This is achieved either by scarf/taper or step sanding the composite structure. Taper/Scarf sanding may require maintaining a constant pre-defined scarf overlap corresponding to a given scarf angle. Example embodiments may be reliable, efficient and precise for each of these different methodologies.

In some cases, relative to employment of scanning technology, it may be difficult to reliably identify edges of plies of the parent material when sanded in a smooth scarf. This occurs because the exposed ply boundaries may have a different cross section of the fibers in the damaged area corresponding to a different ply orientation. Additionally, understanding repair material cured ply thickness is important as the algorithms described herein can only be as accurate as the information given.

An aircraft component may be made from composite materials that are defined by various layers or plies, a sandwich or monolithic construction. For sandwich construction, composite plies are typically bonded to a core using a film adhesive. Damage to the aircraft component may be experienced due to a number of different phenomena. These instances of damage may cause abrasion, denting, puncturing, and/or the like on the aircraft component with varying shapes, depths, contours and the like. Accordingly, the damage may have different impact on each respective layer or ply such that, for example, the profile of any repair patch would need to account for different sized/shaped layers that must each be oriented appropriately relative to a common reference to ensure that the repair patch faithfully corresponds to the damaged area. FIG. 1 illustrates a side view of a damaged area that has received impact damage up to a core 100 material through three layers of composite material including a first ply 110, a second ply 120, and a third ply 130. Impact damage shown is to a sandwich component with facesheet damage only. Impact damage may affect any composite component with or without core. In the case of a sandwich construction, damage may include both core and facesheet. As can be seen from FIG. 1, the contour of the damaged area is such that repair ply layers must have different corresponding diameters. Moreover, a filler ply and an extra ply may be provided to surround the repair plies, which may include materials matching those of the first ply 110, second ply 120, and third ply 130. The same methodology may be used to restore a damaged core.

Figure 2:
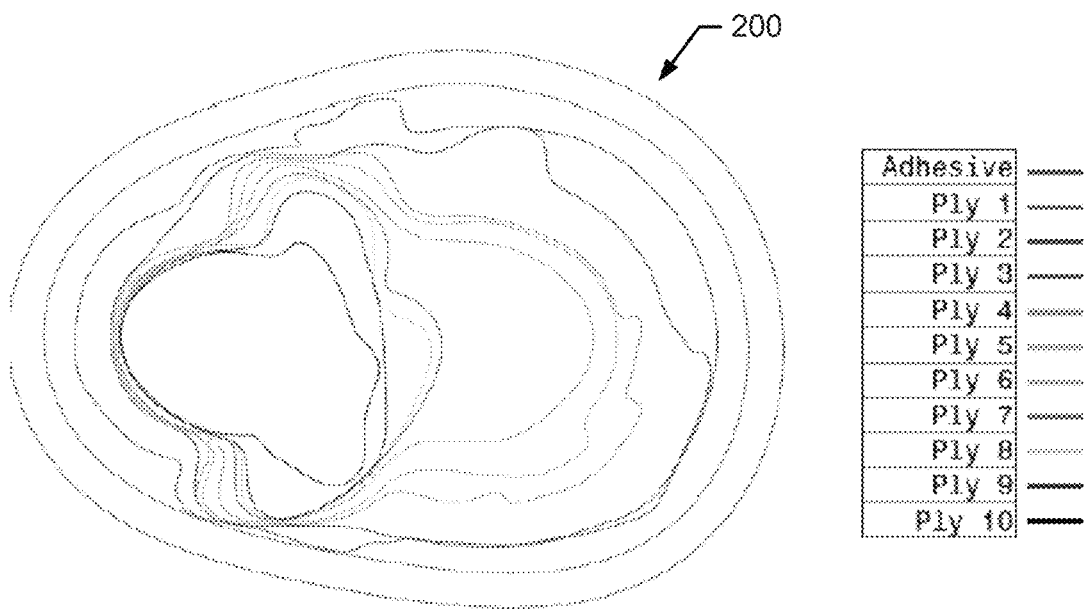
FIG. 2 illustrates a top view of a ply layout for a repair patch according to an example embodiment.

In a simple case where the damaged area was perfectly rounded in shape, the repair plies could simply be cut with their corresponding different diameters, and the repair plies could be coaxially aligned and adhered to make a repair patch. However, as shown in FIG. 2, which is a top view of a ply layout 200 for a repair patch, the shapes of the plies may be very different, and orienting them may be complicated in some cases. If the repair patch cannot be created to accurately correspond to the damaged area in a fast and efficient way, the aircraft may be out of service for a longer period of time and the cost of such downtime may rapidly mount. Thus, a modeling and cutting system of an example embodiment may be provided to enable a repair patch to be generated in a fast, efficient and accurate way.

Figure 3:
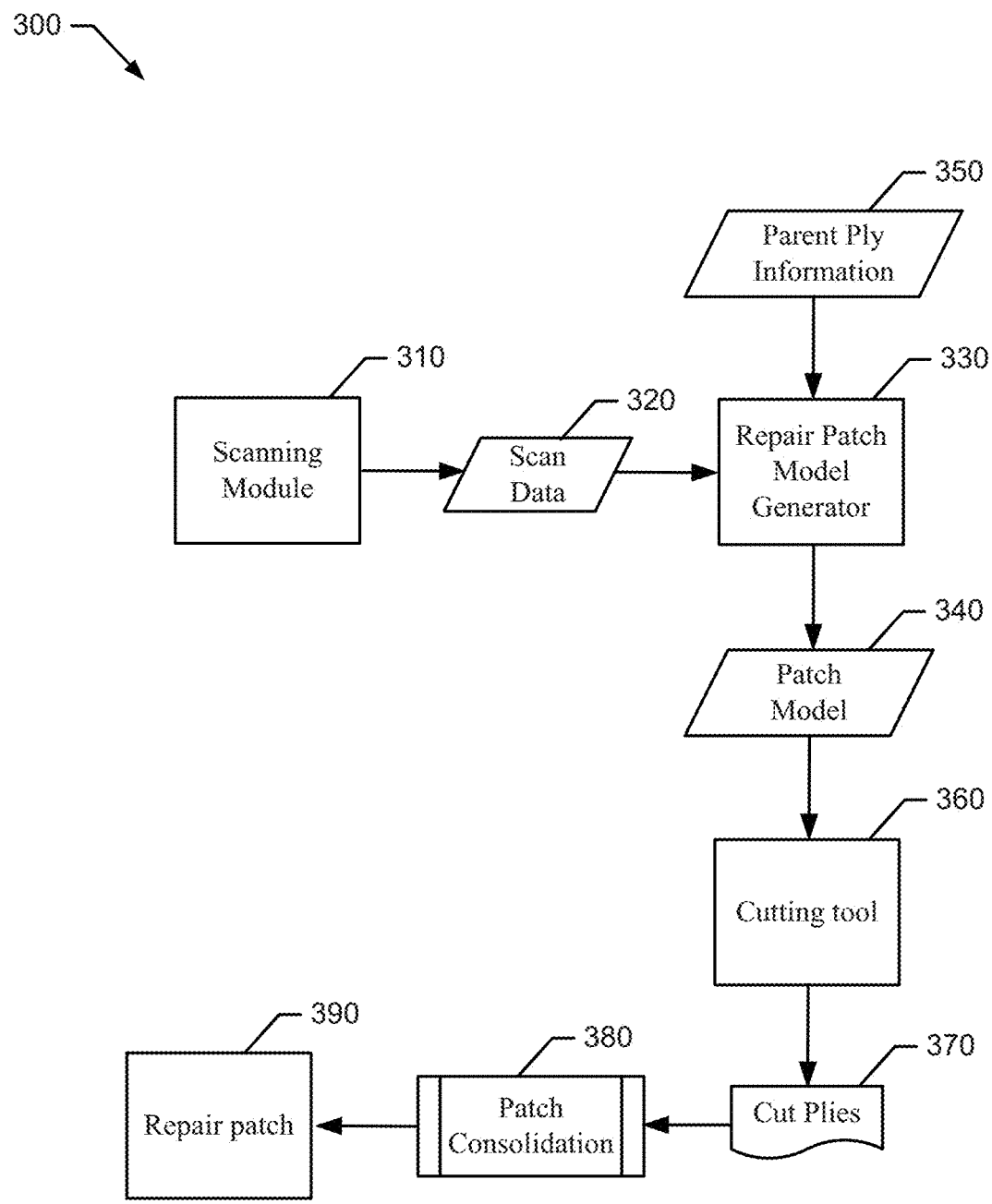
FIG. 3 illustrates a block diagram of a system for performing a repair on composite aircraft component portions in accordance with an example embodiment.

FIG. 3 illustrates a block diagram of a repair patch modeling and generation system in accordance with an example embodiment. As shown in FIG. 3, the system 300 may include a scanning module 310 that may be capable of providing scan data 320 to repair patch model generator 330 that can generate cutting files 340 for provision to a cutting machine 350.

The scanning module 310 may be an optical scanner, or may employ other scanning technologies (e.g., RF scanning, laser scanning, acoustic scanning, and/or the like). In the case of an optical scanner, the scanning module 310 may be configured, for example, to emit light and capture reflections to determine the depth, contour and shape of a damaged area. In some embodiments, the scanning module 310 may employ a hand held scanner that can be passed over the surface of the aircraft at the damaged area to generate scanned data 320 indicative of the damaged area. The scanned data 320 may be stored in local or removable memory. In either case, the scanned data 320 may ultimately be communicated to the repair patch model generator 330. In some cases, the scanning module 310 may be configured to employ wireless or wired communication to transfer the scanned data to the repair patch model generator 330. However, in other cases, the scanned data 320 may be transferred via the removable memory or some other method to another device (e.g., a laptop computer, smart phone, computer terminal and/or the like) so that the other device can transfer the scanned data 320 to the repair patch model generator 330 via wired or wireless communication.

The repair patch model generator 330 may be configured to utilize the scanned data 320 to generate a patch model 340 that includes a multiple ply model of a repair patch that corresponds to the damaged area. In some cases, the repair patch model generator 330 may be provided or otherwise access information indicative of ply ordering of the composite material in the damaged area. This information may be referred to as parent ply information 350. In some cases, a database may be accessed that includes parent ply information 350 for a plurality of aircraft components. Thus, if the aircraft and/or aircraft component at which the damaged area is located can be identified, the database of parent ply information 350 may be accessed to determine the ordering of plies at the damaged area. Given this information, and the scanned data 320, the repair patch model generator 330 may generate the patch model 340.

The patch model 340 may define the shapes of each ply of a repair patch that corresponds to the damaged area based on the scanned data 320. Thus, for example, the patch model 340 may include information indicative of the shapes shown in FIG. 2 for each ply. The patch model 340 may also include the respective depths and contours of the plies needed to properly fill the damaged area shown, for example, in FIG. 1. Moreover, the patch model 340 may indicate the ordering and orientation of each of the plies relative to a common reference axis selected by the repair patch model generator 330. Thereafter, a textile cutting tool 360 (e.g., a Gerber cutter or other ultrasonic cutting machine or textile cutting machine) may be used to cut each respective ply from corresponding sheets of material that match material of each respective ply of the parent ply information 350.

The cutting tool 360 may therefore generate a plurality of cut plies 370. The cut plies 370 may, in some cases, be marked with orientation information or reference axis markings to allow the cut plies to be assembled during patch consolidation 380. Patch consolidation 380 may be accomplished by a tool configured to arrange the plies according to the ply order and orientation alignment information provided in the patch model 340 in order to generate the repair patch 390. However, in other cases, manual patch consolidation may be accomplished. Moreover, in some cases, the plies could be laid up individually at the damaged section with adhesive applied between each ply. A printout or map of the damaged area and the plan for ply placement may be provided to guide the repair operator for ply placement and orientation. In either case, adhesives may be applied between ply layers, where appropriate.

Thus, not only can each of the plies be cut to the corresponding correct size and shape, but the plies can each be ordered and oriented to enable the repair patch 390 to be provided with a very faithful and accurate correlation to the damaged area as indicated in the scanned data 320. Moreover, it should be appreciated that the scanning module 310 may be used on-site where the aircraft is located. However, the scanned data 320 can be communicated to a remote location at which the repair patch model generator 330 is located. The patch model 340 can then be used to generate the cut plies 370 via the cutting tool 360 at the same or a different location as that of the repair patch model generator 330. In some cases, the repair patch model generator 330 and the cutting tool 360 may both be located at a repair center. Patch consolidation 380 can then also be accomplished, for example, at the repair center or on site. The repair patch 390 can then be delivered back to the location of the aircraft so that the repair patch can be applied using composite repair best practices used in composite manufacture and repair of aircraft.

Figure 4:
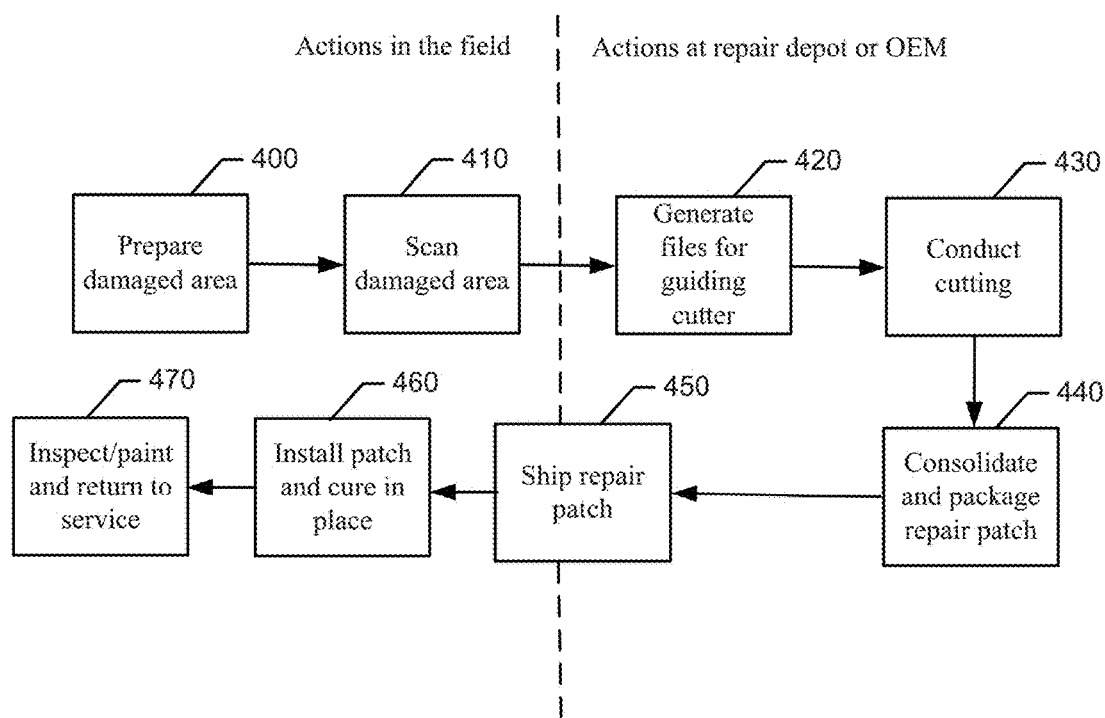
FIG. 4 is a block diagram of a repair process employed in accordance with an example embodiment.

FIG. 4 illustrates a block diagram of a repair process employed in accordance with an example embodiment. As shown in FIG. 4, part of the process may be accomplished in the field, at the location of the damaged aircraft, and part may be accomplished at a repair depot or OEM (original equipment manufacturer). In this regard, for example, initial preparation of the damaged area may be accomplished at operation 400. The initial preparation may include damage removal and scarfing or step grinding, which may further include some cleaning, sanding, grinding, cutting and/or the like to prepare the damaged area for scanning. A pneumatic die grinder with aluminum oxide sandpaper (or equivalent sanding tools) may be used to scarf or step grind the damaged area. Prior to scanning, scarfed sections may be cleaned with approved solvents to remove any foreign materials and carbon fibers particles to ensure good surface preparation prior to bonding later on with the repair patch. Thereafter, the damaged area may be scanned at operation 410. As mentioned above, a scanner may be employed (e.g., as all or part of the scanning module 310). In an example embodiment, a Q-Flash White Light Scanner by Hexagon Metrology may be employed as the scanner. However, other scanners may also be used.

As discussed above, scanned data generated responsive to operation 410 may then be sent to a repair depot or OEM facility at which location files, to cut repair plies, may be generated for guiding a cutter (e.g., cutting tool 360) at operation 420. As mentioned above, a model (e.g., CAD drawings for plies and adhesive) may be sent to the textile cutting tool 360 to produce each of the plies and adhesive. The cutting process may include placing the materials to be cut (e.g., based on the parent ply information 350) on the textile cutter followed by a layer of high density polyethylene (or equivalent) to keep the fabric in place under vacuum during the ply cutting process. The textile cutting tool 360 may be used to cut the required film adhesive layer. The cutting may then be conducted at operation 430 and the plies that have been cut can be consolidated and packaged at operation 440. The repair patch (assembled or ready for assembly) can then be shipped at operation 450 back to the field or location where the repair will take place.

Figure 5:
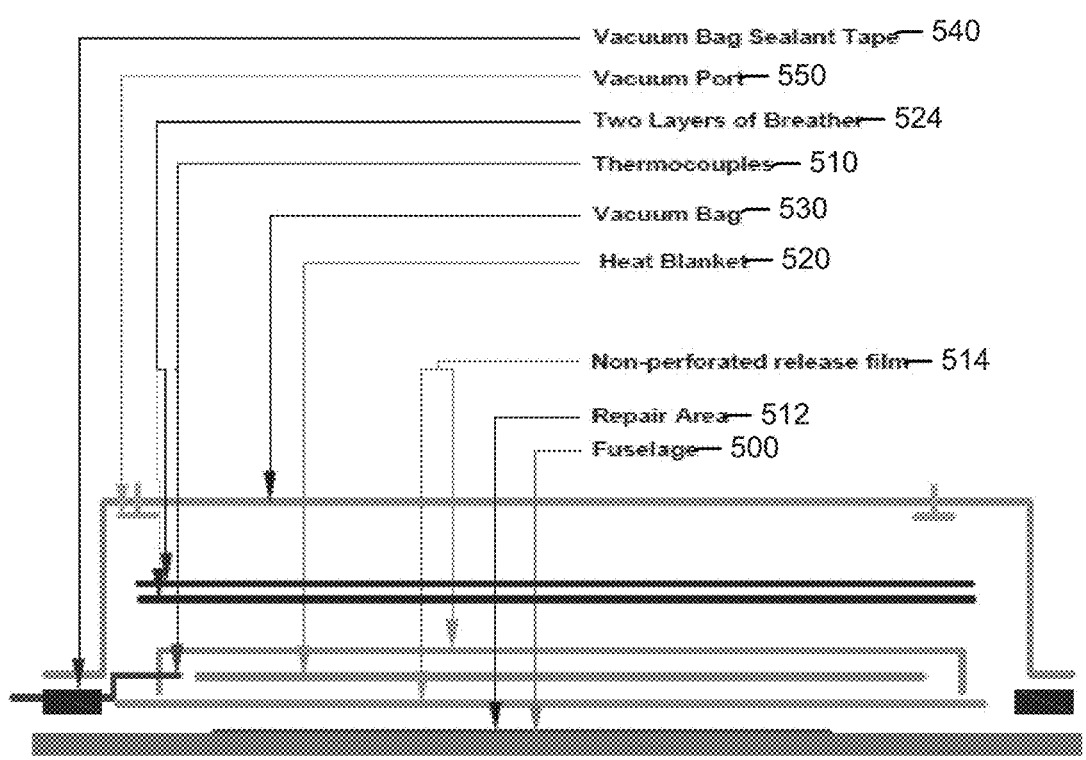
FIG. 5 illustrates a schematic diagram of a representative bagging scheme used during the repair process in accordance with an example embodiment.

At operation 460, the repair patch can be installed and cured in place. An adhesive layer may be placed on the scarfed area prior to laying up the repair plies onto the scarfed surface. FIG. 5 illustrates a schematic diagram of a bagging procedure used during the repair process. The repair is then cured using the appropriate cure cycle for the repair material used. Thereafter, at operation 470, the repair can be inspected and the aircraft may be returned to service.

In an example embodiment, as shown in FIG. 5, a composite part 500 may have the plies laid up thereon and one or more (e.g., at least four in some cases) thermocouples 510 may be placed around the repair region 512 to monitor temperature around the repair during curing. A non-perforated release film 514 may be placed over the repair region 512 followed by a heat blanket 520, another layer of non-perforated release film 514 and two layers of breather 524 as shown in FIG. 5. Of note, FIG. 5 illustrates a representative bagging scheme and it should be appreciated that a corresponding scheme specified for the repair material utilized would be used in other examples. A vacuum bag 530 may then be placed over the entire area and sealed with sealant 540. A vacuum port 550 may then be employed to enable a vacuum to be drawn for the curing process. The repair may be cured using the two step cure cycle 600 shown in FIG. 6.

Figure 6:
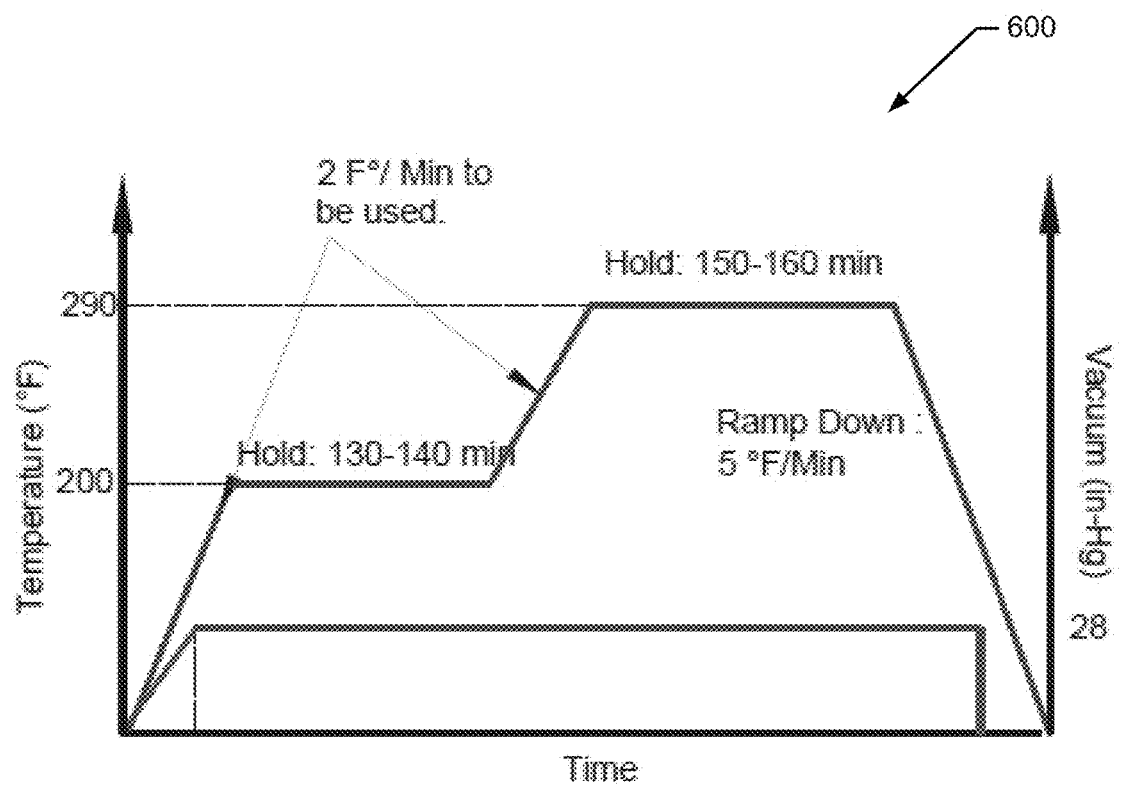
FIG. 6 illustrates a representative cure cycle that may be employed in a repair process in accordance with an example embodiment (dependent on repair material)

As shown in FIG. 6, temperature may initially be raised and monitored by the thermocouples 510 to achieve a temperature of about 200 degrees F. Temperature may be raised at a rate of about 2 degrees per minute. Thereafter, temperature may be held at 200 degrees for about 130 to 140 minutes before another temperature increase at a rate of about 2 degrees per minute is initiated. Temperature may be raised until a temperature of about 290 degrees F. is reached. This temperature may then be held for about 150 to 160 minutes before temperature is ramped downward at a rate of about 5 degrees per minute. As noted by FIG. 6, the cycle may be performed under a vacuum. Of note, FIG. 6 illustrates a representative cure cycle and it should be appreciated that a corresponding cure cycle specified for the repair material utilized would be used in other examples.

Figure 7:
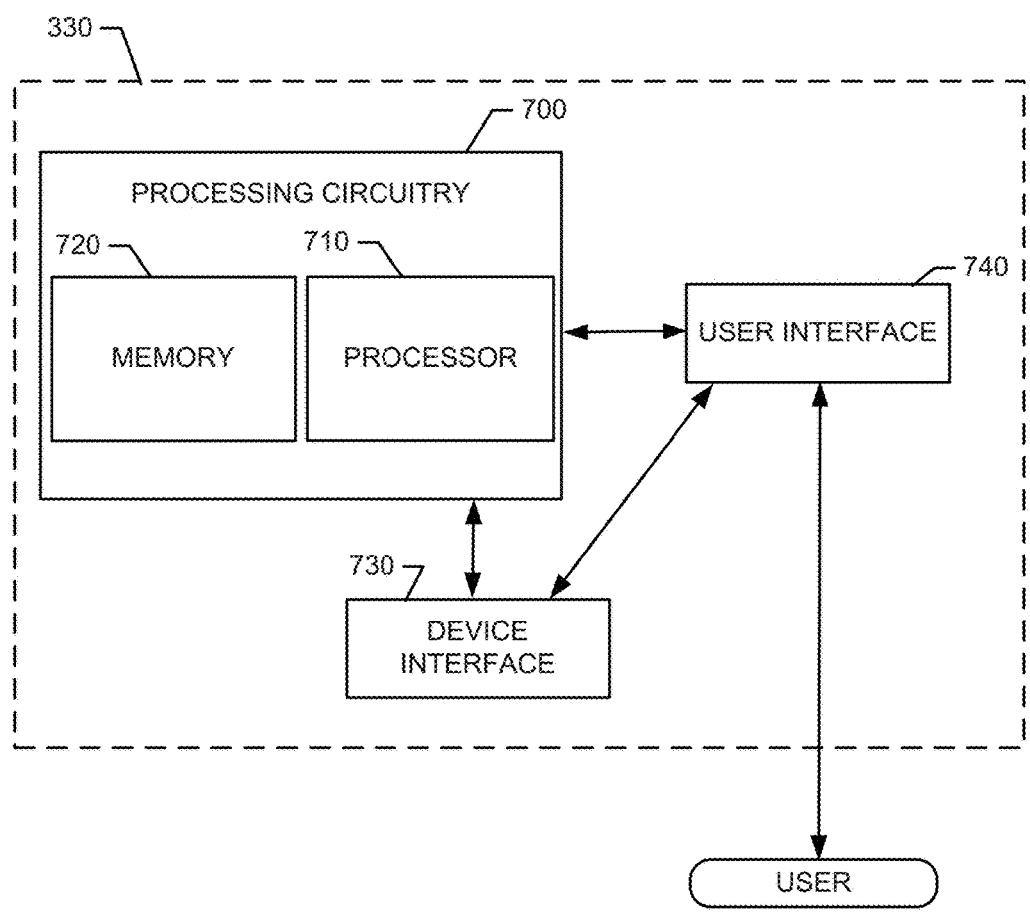
FIG. 7 illustrates a block diagram of an example structure that may be employed to embody a repair patch model generator according to an example embodiment.

In some cases, the repair patch model generator 330 may employ processing circuitry that is configured to generate the patch model 340 based on the scanned data 320 and the parent ply information 350. An example of structure that may be employed to embody the repair patch model generator 330 of an example embodiment is shown in FIG. 7. The repair patch model generator 330 may include or otherwise be in communication with the processing circuitry 700 that is configurable to perform actions in accordance with example embodiments described herein. As such, for example, at least some of the functions attributable to the repair patch model generator 330 may be carried out by or otherwise instructed by the processing circuitry 700. The processing circuitry 700 may provide the hardware that is programmed or that hosts software to configure the system for model generation techniques consistent with example embodiments. In this regard, generation of the patch model 340 may therefore be accomplished using the processing circuitry 700.

The processing circuitry 700 may be configured to perform data processing, control function execution and/or other processing and management services according to an example embodiment of the present invention. In some embodiments, the processing circuitry 700 may be embodied as a chip or chip set. In other words, the processing circuitry 700 may comprise one or more physical packages (e.g., chips) including materials, components and/or wires on a structural assembly (e.g., a baseboard).

In an example embodiment, the processing circuitry 700 may include one or more instances of a processor 710 and memory 720 that may be in communication with or otherwise control a device interface 730 and, in some cases, a user interface 740. As such, the processing circuitry 700 may be embodied as a circuit chip (e.g., an integrated circuit chip) configured (e.g., with hardware, software or a combination of hardware and software) to perform operations described herein.

The user interface 740 (if implemented) may be in communication with the processing circuitry 700 (directly or via the device interface 730) to receive an indication of a user input at the user interface 740 and/or to provide an audible, visual, mechanical or other output to the user. As such, the user interface 740 may include, for example, a display, one or more buttons or keys (e.g., function buttons), and/or other input/output mechanisms (e.g., keyboard, microphone, speakers, cursor, joystick, lights and/or the like). The user interface 740 may display or otherwise provide an output of information indicating characteristics of a data set (e.g., sensor data and/or model data). Moreover, in some cases, the user interface 740 may include options for selection of one or more reports to be generated based on the analysis of a given data set.

The device interface 730 (if employed) may include one or more interface mechanisms for enabling communication with the various internal and/or external devices of the repair patch model generator 330 and/or with which the repair patch model generator 330 communicates. In some cases, the device interface 730 may be any means such as a device or circuitry embodied in either hardware, or a combination of hardware and software that is configured to receive and/or transmit data from/to devices in communication with the processing circuitry 700. In some cases, the device interface 730 may include one or more ports for external component connectivity and/or communication. Standard ports such as USB, other data ports, or power cable ports may be provided. However, in some cases, the ports may be for proprietary connectivity mechanisms. Wireless or wired communication may also be supported by the device interface 730. Thus, in some cases the device interface 730 may include an antenna and/or radio circuitry for communication according to a wireless communication protocol, or means for communicating with and/or connecting to the Internet.

In an exemplary embodiment, the memory 720 may include one or more non-transitory memory devices such as, for example, volatile and/or non-volatile memory that may be either fixed or removable. The memory 720 may be configured to store information, data, applications, instructions or the like for enabling the repair patch model generator 330 to carry out various functions in accordance with exemplary embodiments of the present invention. For example, the memory 720 could be configured to buffer input data for processing by the processor 710. Additionally or alternatively, the memory 720 could be configured to store instructions for execution by the processor 710. As yet another alternative, the memory 720 may include one or more databases that may store a variety of data sets indicative of features or characteristics of data that can be correlated to corresponding parameters. For example, data captured by the scanning module 310 may be correlated to the parent ply information 350 to determine which materials belong in each layer or ply of the scanned data. Among the contents of the memory 720, applications may be stored for execution by the processor 710 in order to carry out the functionality associated with each respective application. In some cases, the applications may include directions for generating a model based on scanned data. In some cases, the applications may further include directions for generating outputs and/or reports associated with analysis of data as described herein.

The processor 710 may be embodied in a number of different ways. For example, the processor 710 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 710 may be configured to execute instructions stored in the memory 720 or otherwise accessible to the processor 710. As such, whether configured by hardware or by a combination of hardware and software, the processor 710 may represent an entity (e.g., physically embodied in circuitry—in the form of processing circuitry 700) capable of performing operations according to embodiments of the present invention while configured accordingly. Thus, for example, when the processor 710 is embodied as an ASIC, FPGA or the like, the processor 710 may be specifically configured hardware for conducting the operations described herein. Alternatively, as another example, when the processor 710 is embodied as an executor of software instructions, the instructions may specifically configure the processor 710 to perform the operations described herein.

In an example embodiment, the processor 710 (or the processing circuitry 700) may be embodied as, include or otherwise control the repair patch model generator 330 (or components thereof). As such, in some embodiments, the processor 710 (or the processing circuitry 700) may be said to cause each of the operations described in connection with the repair patch model generator 330 (or components thereof) by directing the repair patch model generator 330 (or respective components) to undertake the corresponding functionalities responsive to execution of instructions or algorithms configuring the processor 710 (or processing circuitry 700) accordingly.

Figure 8:
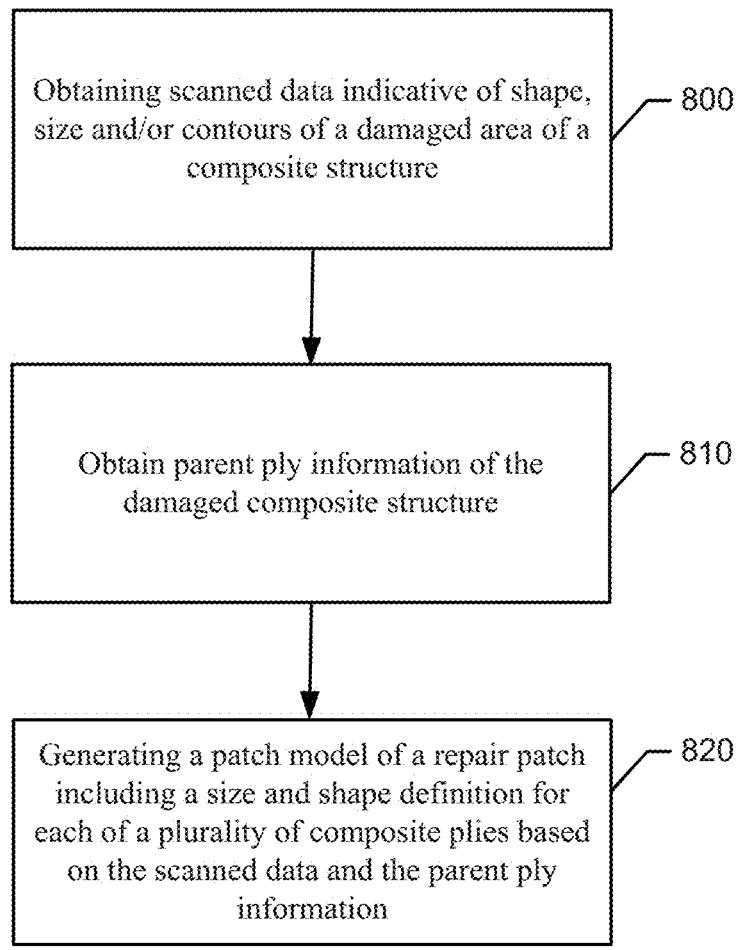
FIG. 8 illustrates a block diagram of a method of generating a repair patch for a damaged area of an aircraft according to an example embodiment.

From a technical perspective, the platform described in FIG. 7 may be used to facilitate the implementation of several computer based interactions that improve the functioning and efficiency of the computer for analyzing data and generating a model of a repair patch as described herein. As an example, FIG. 8 is a flowchart of a method and program product according to an example embodiment of the invention. It will be understood that each block of the flowchart, and combinations of blocks in the flowchart, may be implemented by various means, such as hardware, firmware, processor, circuitry and/or other device associated with execution of the instructions and/or operations described herein. For example, one or more of the procedures described may be embodied by computer program instructions. These computer program instructions may also be stored in a computer-readable memory that may direct a computer or other programmable apparatus to function in a particular manner, such that the instructions stored in the computer-readable memory produce an article of manufacture which implements the functions specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method of generating a repair patch for a damaged area of an aircraft or other composite structure is provided. The method may include obtaining scanned data indicative of a shape, size and/or contours of the damaged area of a composite structure at operation 800, obtaining parent ply information of the damaged composite structure at operation 810, and generating a patch model of a repair patch including size and shape definition for each of a plurality of plies based on the scanned data and the parent ply information at operation 820.

In an example embodiment, an apparatus for performing the method of FIG. 8 above may comprise a processor or processing circuitry configured to perform some or each of the operations (800-820) described above. The processor may, for example, be configured to perform the operations (800-820) by performing hardware implemented logical functions, executing stored instructions, or executing algorithms for performing each of the operations. In some embodiments, the processor or processing circuitry may be further configured for additional operations or optional modifications to operations 800 to 820. In this regard, for example, the method may further include the patch model being provided to a cutter configured to cut each of the plies based on the patch model. A textile cutter may be used. In an example embodiment, obtaining the scanned data may include obtaining the scanned data from wireless or wired communication, or from a removable memory device. In some cases, obtaining the parent ply information may include retrieving the parent ply information from a database storing composite structure ply information for each of a plurality of aircraft or aircraft components. In an example embodiment, the patch model may include orientation information and order information to enable the plies to be assembled as the repair patch to repair the damaged area.

In some cases, tasks associated with performing an example embodiment may include generating a scanning management plan including an indexing and reference axis that can be used for repair patch positioning. Data from the scanned surface may be moved into a 3-D drawing system, then output to a Gerber cutter subsequently used to cut repair plies. The repair plies may then be stacked according to the parent ply database information and then used to repair the damaged areas using field repair techniques and equipment.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A system for generating a repair patch for a damaged area of a composite structure, the system comprising:
 a scanning module deployable on-site at a location of the composite structure, the scanning module being configured to scan the damaged area to generate scanned data indicative of a shape, size and/or contours of the damaged area;

a repair patch model generator comprising processing circuitry configured to:
  obtain the scanned data;
  obtain parent ply information of the composite structure; and
  generate a patch model of a repair patch including size and shape definition for each of a plurality of plies based on the scanned data and the parent ply information, wherein the patch model is generated on-site at the location of the composite structure; and
a cutting tool located remote from the location of the composite structure and configured to receive cutting files based on the patch model to generate a plurality of cut plies that are separately cut and assembled remote from the location of the composite structure to form the repair patch for delivery to the location of the composite structure,
wherein the patch model includes orientation information defined relative to a common reference axis for each ply and order information to enable the plies to be oriented and assembled as the repair patch to repair the damaged area.

2. The system of claim 1, wherein the cutting tool is a textile cutting machine.

3. The system of claim 1, wherein receiving the cutting files comprises receiving the cutting files via wireless or wired communication, or via a removable memory device.

4. The system of claim 1, wherein obtaining the parent ply information comprises retrieving the parent ply information from a database storing composite structure ply information for each of a plurality of aircraft or aircraft components.

5. The system of claim 1, wherein upon the repair patch being generated at the location remote from the composite structure, the repair patch is transported to the location of the composite structure for installation.

6. The system of claim 5, wherein the repair patch is installed and cured at the composite structure under vacuum.

7. The system of claim 1, wherein the orientation information is printed on each ply.

8. A method of generating a repair patch for a damaged area of a composite structure, the method comprising:
  obtaining scanned data indicative of a shape, size and/or contours of the damaged area of the composite structure;
  obtaining parent ply information of the composite structure; and
  generating a patch model of a repair patch including size and shape definition for each of a plurality of plies based on the scanned data and the parent ply information, wherein the patch model is generated on-site at the location of the composite structure; and
  providing cutting files based on the patch model to a cutting tool that is located remote from the location of the composite structure and configured to receive the cutting files based on the patch model to generate a plurality of cut plies that are separately cut and assembled remote from the location of the composite structure to form the repair patch for delivery to the location of the composite structure,
  wherein generating the patch model includes generating the patch model to include orientation information defined relative to a common reference axis for each ply and order information to enable the plies to be oriented and assembled as the repair patch to repair the damaged area.

9. The method of claim 8, wherein the cutting tool is a textile cutting machine.

10. The method of claim 8, wherein providing the cutting files comprises providing the cutting files via wireless or wired communication, or via a removable memory device.

11. The method of claim 8, wherein obtaining the parent ply information comprises retrieving the parent ply information from a database storing composite structure ply information for each of a plurality of aircraft or aircraft components.

12. The method of claim 8, wherein in response to generating the repair patch at the location remote from the composite structure, the repair patch is transported to the location of the composite structure for installation.

13. The method of claim 12, wherein the repair patch is installed and cured at the composite structure under vacuum.

14. The method of claim 8, wherein generating the patch model further includes printing the orientation information on each ply.

* * * * *